(12) United States Patent
Mansson et al.

(10) Patent No.: US 9,272,983 B2
(45) Date of Patent: *Mar. 1, 2016

(54) 2-AMINO-3-METHYL-HEX-5-ENOIC ACID AND ITS USE IN THE PRODUCTION OF PEPTIDES INCLUDING BACITRACINS

(75) Inventors: Martin Mansson, Oslo (NO); Christine Senstad, Hosle (NO); Jon Efskind, Oslo (NO); Vidar Bjornstad, Sorumsand (NO)

(73) Assignee: XELLIA PHARMACEUTICALS APS (DK)

( * ) Notice: Subject to any disclaimer, the term of this patent is extended or adjusted under 35 U.S.C. 154(b) by 384 days.

This patent is subject to a terminal disclaimer.

(21) Appl. No.: 13/502,144

(22) PCT Filed: Sep. 30, 2010

(86) PCT No.: PCT/EP2010/064511
§ 371 (c)(1),
(2), (4) Date: Apr. 16, 2012

(87) PCT Pub. No.: WO2011/051071
PCT Pub. Date: May 5, 2011

(65) Prior Publication Data
US 2012/0202968 A1    Aug. 9, 2012

Related U.S. Application Data

(60) Provisional application No. 61/255,521, filed on Oct. 28, 2009.

(51) Int. Cl.
*C07C 229/00* (2006.01)
*C07C 229/08* (2006.01)
*C07C 229/30* (2006.01)
*C07K 7/58* (2006.01)

(52) U.S. Cl.
CPC ............ *C07C 229/08* (2013.01); *C07C 229/30* (2013.01); *C07K 7/58* (2013.01)

(58) Field of Classification Search
CPC ..................................................... C07C 229/08
USPC ........................................................ 562/553
See application file for complete search history.

(56) References Cited

U.S. PATENT DOCUMENTS 8,410,044 B2    4/2013   Mansson et al.

FOREIGN PATENT DOCUMENTS

WO    97/47313    12/1997

OTHER PUBLICATIONS

I. Wilson, F.W. Jackson, "Palladium (0) catalysed and copper (I) promoted reactions of secondary zinc reagent derived from L-threonine", Journal of the chemical society, Perkin Transactions 1, Nov. 19, 2002 pp. 2845-2850.
Achmatowicz et al.; "Reaction of the Active C=N-Group with Alkenes: Synthesis of γoδ-Unsturated α-Amino-acids"; J.C.S. Chem. Comm.; p. 484; (1976).
EP2493843; Application 10759663.7Third Party Observation for Application No. #P20100759663; Sep. 22, 2015; 3 pages.

*Primary Examiner* — David Lukton
(74) *Attorney, Agent, or Firm* — Cantor Colburn LLP

(57) ABSTRACT

The present invention concerns 2-amino-3-methyl-hex-5-enoic acid, its use for the production of peptides such as bacitracins and a method for producing it.

8 Claims, 5 Drawing Sheets

2-AMINO-3-METHYL-HEX-5-ENOIC ACID AND ITS USE IN THE PRODUCTION OF PEPTIDES INCLUDING BACITRACINS

This application is a national stage entry of PCT/EP10/64511, filed Sep. 30, 2010, which claims priority to provisional application 61/255,521, filed Oct. 28, 2009.

FIELD OF THE INVENTION

The present invention relates to new amino acid compounds.

BACKGROUND OF THE INVENTION

The majority of proteins are made of 20 different α-amino acids: Alanine, Arginine, Asparagine, Aspartic acid, Cysteine, Glutamine, Glutamate, Phenylalanine, Glycine Histidine, Isoleucine, Lysine, Leucine, Methionine, Proline, Serine, Threonine, Tryptophan, Tyrosine and Valine.

However, there are many biologically active peptides comprising other amino acids such as: Homocysteine, Ornithine, 4-Hydroxyproline, 5-Hydroxylysine, Selenocysteine, Formylmethionin, Phosphoserine, Acetylserine, Methylarginine etc.

Amino acids in D-configuration are common in non-ribosomally synthesized bacterial peptides and less common in ribosomally synthesized proteins. For example in the non-ribosomally synthesized Bacitracins, the amino acid residues in positions 4, 7, 9 and 11 are usually in D-configuration (Glu, Orn, Phe and Asp).

Bacitracins are peptide antibiotics naturally produced by *Bacillus subtilis* and *Bacillus licheniformis*. Several Bacitracins have been identified of which Bacitracin A is of primary importance and is highly active (Biochemistry, vol. 39 no 14, 2000, page 4037-45 by Epperson and Ming). The primary structure of Bacitracin A is $NH_2$-L-Ile$_1$-L-Thiazoline$_2$-L-Leu$_3$-D-Glu$_4$-L-Ile$_5$-L-Lys$_6$-D-Orn$_7$-L-Ile$_8$-D-Phe$_9$-L-His$_{10}$-D-Asp$_{11}$-L-Asn$_{12}$-COOH which is cyclized between the ε-amino group of L-Lys$_6$ and the R-carboxyl group of L-Asn$_{12}$.

Several non-ribosomally synthesized peptides comprise unusual amino acids. For example cyclosporin A comprises 2(S)-amino-3(R)-hydroxy-4(R)-methyl-6(E)-octenoic acid which is crucial for binding to the intracellular receptor for cyclophilin, and thus for its immunosuppressive activity (Journal of Biological Chemistry, vol. 268 no 35, 1993 by Offenzeller et al).

Several uncommon amino acids resemble the structure of Isoleucine:

2-Amino-5-methyl-5-hexenoic acid, a new methionine analog, was isolated from a fermentation broth of *Streptomyces* (Journal of Antibiotics vol. 32 no. 11, page 1118-1124, 1979 by Takeuchi et al).

4 methylene-norleucine and 2-aminohept-6-enoic acid are compounds with the formula: $C_7H_{13}NO_2$.

4 methyl-norleucine is an isoleucine derivative which can be incorporated into a recombinant protein. (J Pharm Biomed Anal, vol 31. no. 5, 2003, page 979-987 by Muramatsu et al).

2-amino-3-methyl-4-pentenoic acid is an unsaturated isoleucine analogue which can be incorporated into proteins (Chembiochem vol. 7 no. 1, 2006, page 83-87 by Mock et al).

The unsaturated norleucines of *Amanita solitaria*. Chemical and pharmacological studies (Lloydia vol. 36 no. 2, 1973, page 69-73 by Chilton et al).

Beta-methylnorleucine, an antimetabolite produced by *Serratia marcescens* (J Antibiot, vol. 34 no. 10, 1981 page 1278-82 by Sugiura et al)

U.S. Pat. No. 6,168,912 describes various allyl derivatives of amino acids for use in a multidimensional combinatorial chemical library.

Allylglycine and crotylglycine are described in Journal of Bacteriology, vol. 148 no. 1, 1981 by Kunz et al.

SUMMARY OF THE INVENTION

The invention concerns the compound 2-amino-3-methyl-hex-5-enoic acid.

Although we use the name 2-amino-3-methyl-hex-5-enoic acid, it covers the same compound as 2-amino-3-methyl-5-hexenoic acid.

The structure of this amino acid compound in its free form is represented by Formula I:

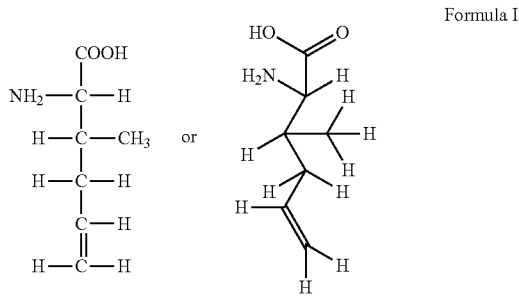

Formula I is not to be interpreted as a Fischer projection, but rather as a compound without specification of stereochemistry.

The amino acid of Formula I comprises two chiral carbon atoms. The present invention covers the four stereoisomers of 2-amino-3-methyl-hex-5-enoic acid:
(2S,3S)-2-amino-3-methyl-hex-5-enoicacid,
(2R,3S)-2-amino-3-methyl-hex-5-enoic acid,
(2S,3R)-2-amino-3-methyl-hex-5-enoic acid, and
(2R,3R)-2-amino-3-methyl-hex-5-enoic acid.

Further, the present invention covers salts and ions of 2-amino-3-methyl-hex-5-enoic acid.

Further, the present invention covers amino protected and carboxy protected derivatives of 2-amino-3-methyl-hex-5-enoic acid.

We propose and use the name 5-Methylene-Isoleucine for 2-amino-3-methyl-hex-5-enoic acid. Accordingly, the 5-Methylene-Isoleucine side chain has the structure —$CH(CH_3)CH_2CH=CH_2$ which could be represented The invention also concerns use of 5-Methylene-Isoleucine for producing Bacitracins and a process for making 5-Methylene-Isoleucine.

5-Methylene-Isoleucine can be used for production of Bacitracin J1, Bacitracin J2, Bacitracin J3, Bacitracin K1, Bacitracin K2, Bacitracin K3 and Bacitracin L.

The aspects of the invention may be obtained by the features as set forth in the following description of the invention and/or the appended patent claims.

DETAILED DESCRIPTION OF THE INVENTION

Some highly active Bacitracins comprise an uncommon amino acid side chain which has the following structure:

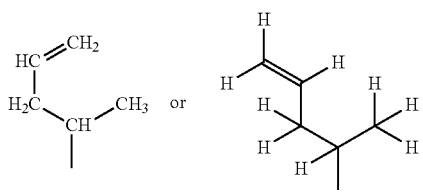

We have proposed and use the names Bacitracin J, K or L for Bacitracins comprising structure above. The structures of these Bacitracins are represented in FIG. 1A-G.

DEFINITIONS

Figure 1A:
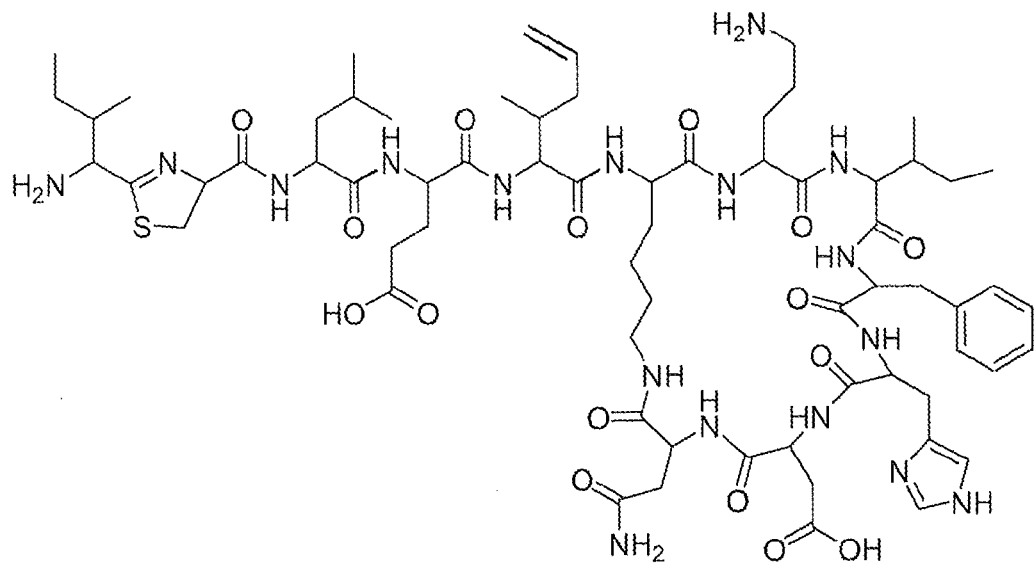
FIG. 1A shows the structure of Bacitracin with a 5-Methylene-Isoleucine residue in position 5 (=Bacitracin J1).
Figure 1B:
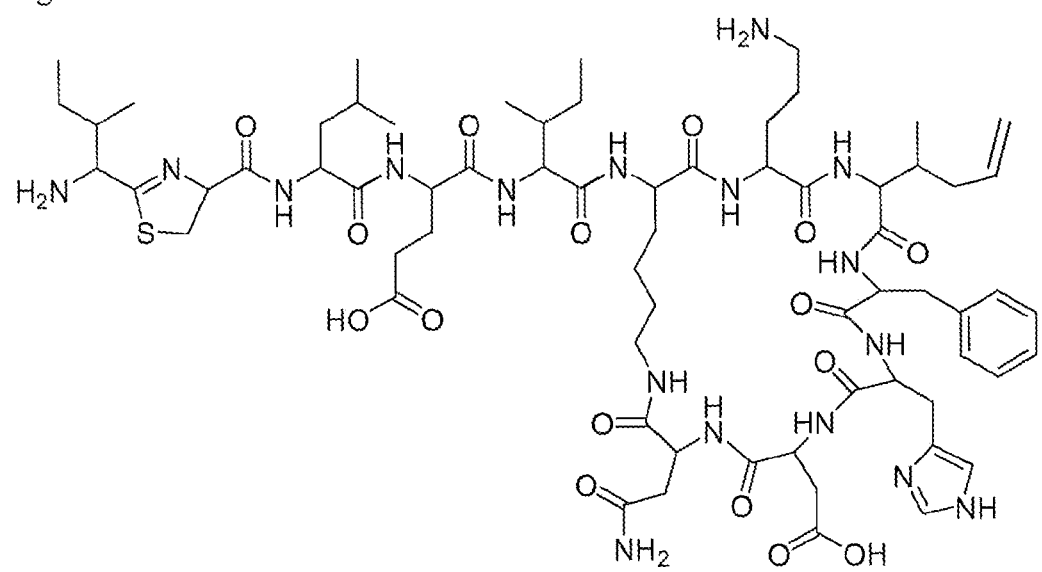
FIG. 1B shows the structure of Bacitracin with a 5-Methylene-Isoleucine residue in position 8 (=Bacitracin J2).
Figure 1C:
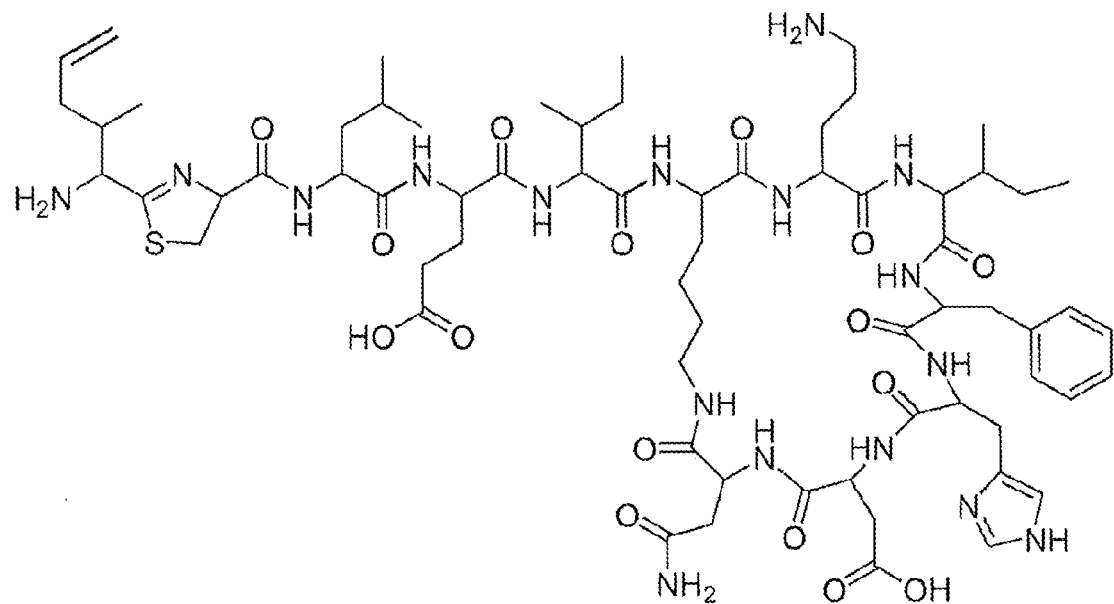
FIG. 1C shows the structure of Bacitracin with a 5-Methylene-Isoleucine residue in position 1 (=Bacitracin J3).
Figure 1D:
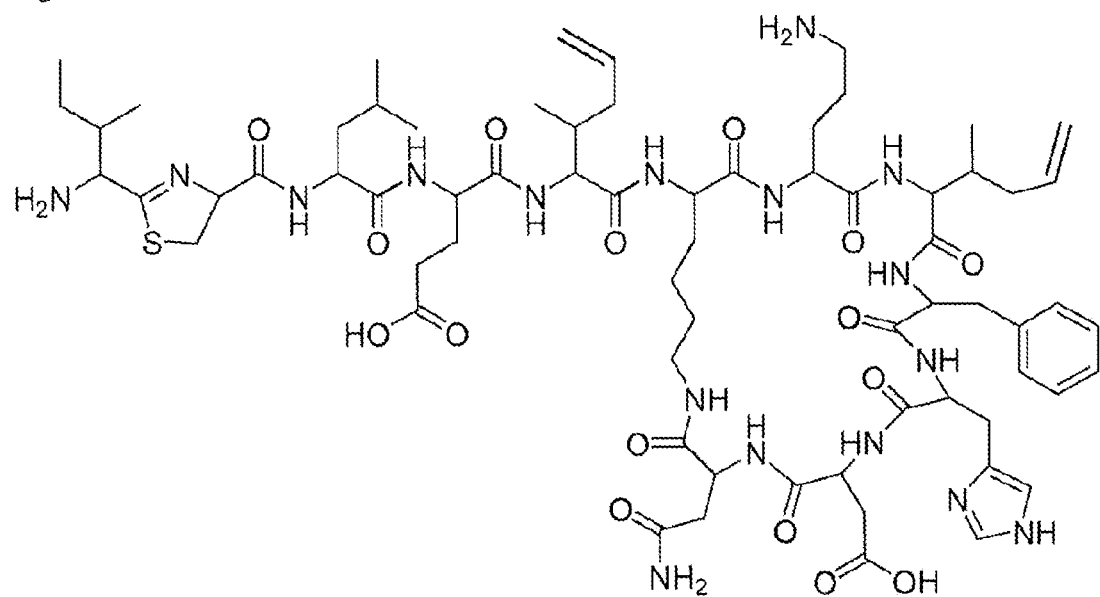
FIG. 1D shows the structure of Bacitracin with 5-Methylene-Isoleucine residues in position 5 and 8 (=Bacitracin K1).
Figure 1E:
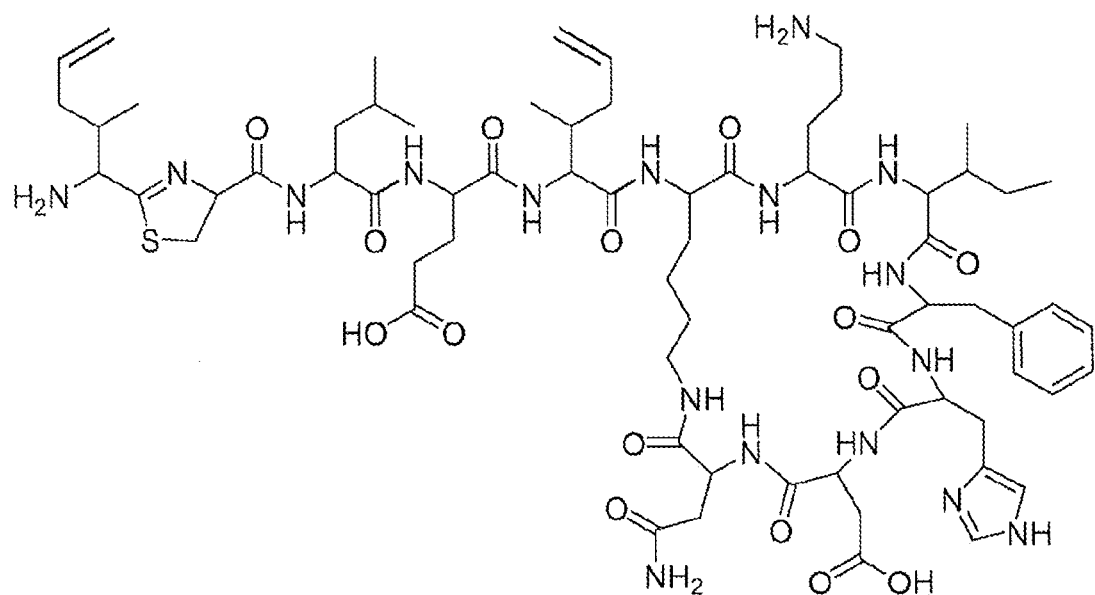
FIG. 1E shows the structure of Bacitracin with 5-Methylene-Isoleucine residues in position 1 and 5 (=Bacitracin K2).
Figure 1F:
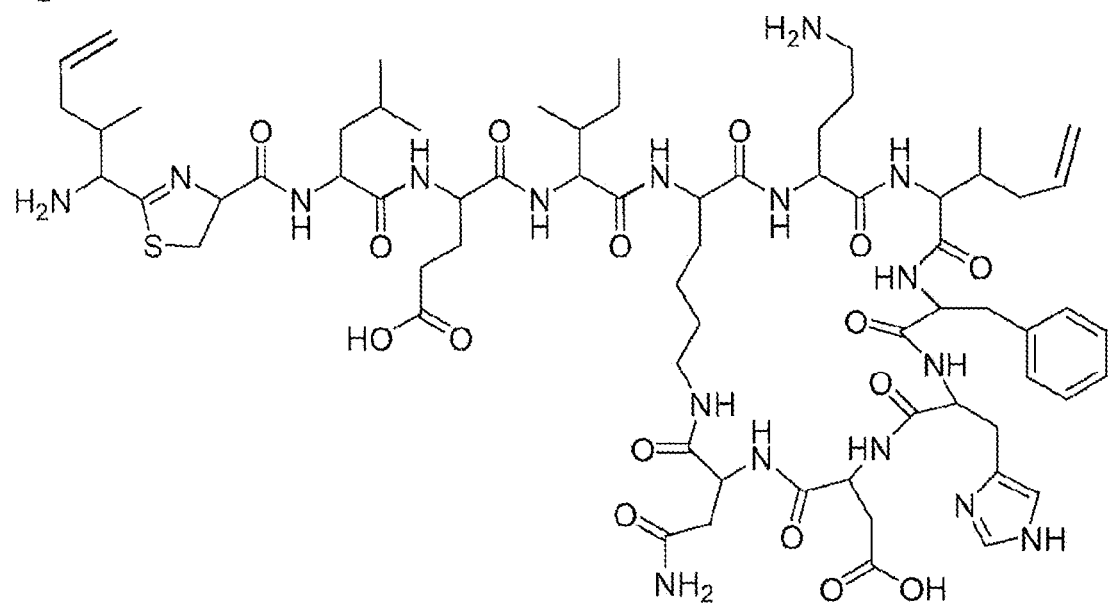
FIG. 1F shows the structure of Bacitracin with 5-Methylene-Isoleucine residues in position 1 and 8 (=Bacitracin K3).
Figure 1G:
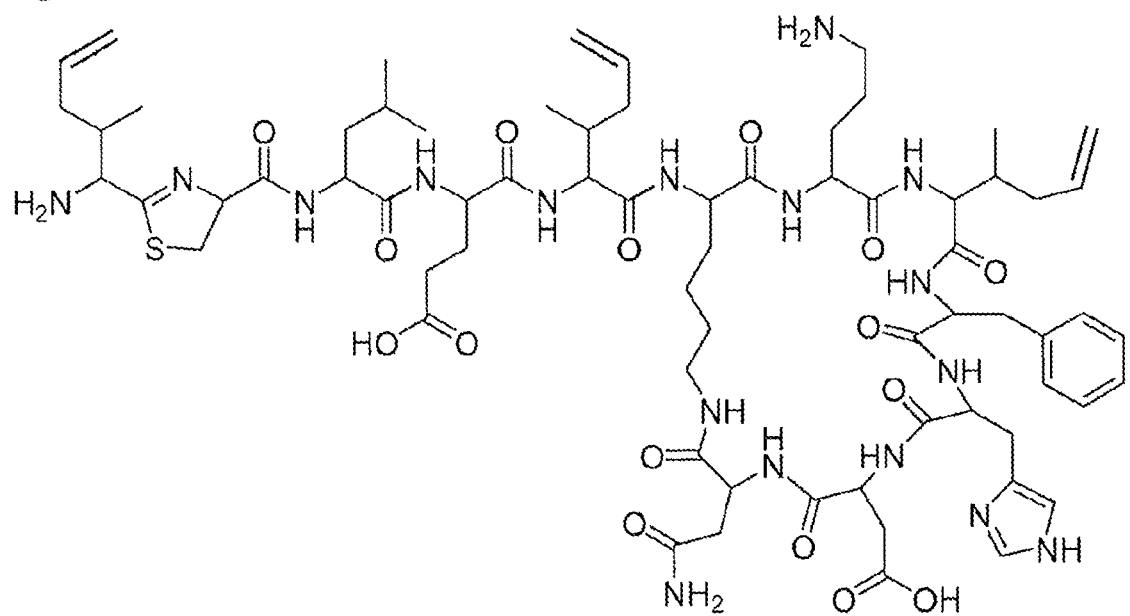
FIG. 1G shows the structure of Bacitracin with 5-Methylene-Isoleucine residues in position 1, 5 and 8 (=Bacitracin L).
Figure 2:
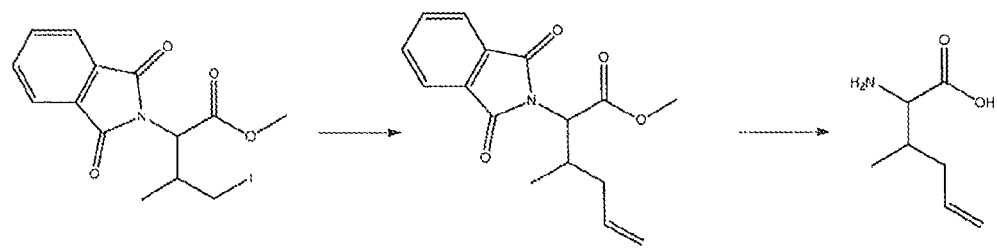
FIG. 2 shows a route for production of 5-Methylene-Isoleucine as disclosed in the examples.
Figure 3:
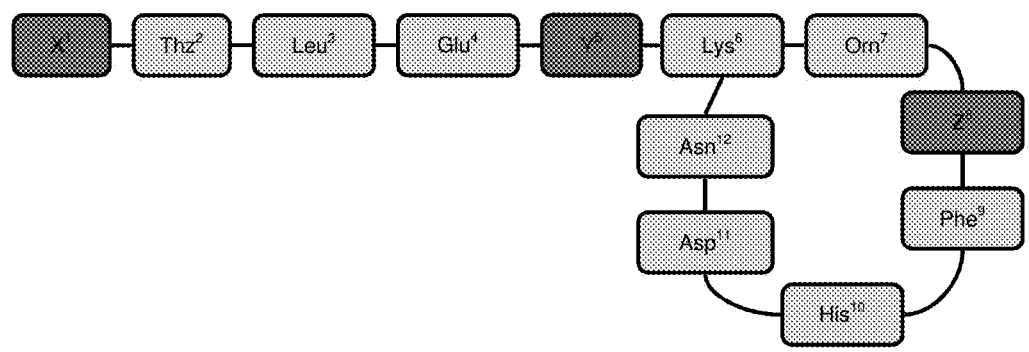
FIG. 3 is the structure of a bacitracin.

"Bacitracins" are peptide compounds comprising the structure of FIG. 3 (with amino acid residue numbering in superscript):
wherein X is

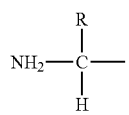

and, wherein R is the side chain of the amino acid residue of Isoleucine, Valine or 5-Methylene-Isoleucine;
and wherein
Y and Z are independently
the amino acid residue of
Isoleucine, Valine or 5-Methylene-Isoleucine;
and wherein
Thz is a Thiazoline ring

2' coupled to X and 4' coupled to the α-carbon in Leu;
and wherein
Leu is a Leucine amino acid residue
Glu is a Glutamine amino acid residue
Lys is a Lysine amino acid residue forming peptide bonds with Y and Orn while its
ε-amine is coupled to the α-carboxyl group of Asparagine by a peptide bond
Orn is an Ornithine amino acid residue
Phe is a Phenylalanine amino acid residue
His is a Histidine amino acid residue
Asp is an Aspartic acid amino acid residue
Asn is an Asparagine amino acid residue forming peptide bond with Asp while its
α-carboxyl group is coupled to the ε-amine of Lysine by a peptide bond.

When used in this application; "Bacitracins" is meant to embrace any compound having the primary structure of FIG. 3 regardless of the production method. Thus, the term "Bacitracins" includes the antibiotic compounds naturally produced by *Bacillus licheniformis* but also in vitro produced compounds (synthetic) and semisynthetic compounds having the primary structure of FIG. 3. "Bacitracins" is also meant to embrace any compound having the primary structure above regardless of the charge which varies with pH. "Bacitracins" is also meant to embrace any compound having the primary structure above regardless of the stereochemistry. "Bacitracins" is also meant to embrace salts and hydrates of the compounds having the primary structure of FIG. 3.

"Bacitracins comprising at least one 5-Methylene-Isoleucine residue" is meant to embrace any Bacitracin comprising the structure that would be generated if a Isoleucine or Valine residue(s) was substituted with 5-Methylene-Isoleucine residue(s) in position 1 and/or 5 and/or 8.

When the N-terminal amino group and/or the Thiazoline ring of Bacitracins is oxidized, a substantial amount of the antibacterial activity is lost. For example the low activity compound Bacitracin F, comprises a keto-thiazole moiety instead of the amino-thiazoline moiety (J. Org. Chem, vol. 22, 1957, page 1345-1353 by Craig et al).

"Amino acid" is any compound comprising both an amine and a carboxyl group. Most proteins are built as a linear polymer of 20 different standard α-amino acids in L-configuration: Alanine, Arginine, Asparagine, Aspartic acid, Cysteine, Glutamine, Glutamate, Phenylalanine, Glycine Histidine, Isoleucine, Lysine, Leucine, Methionine, Proline, Serine, Threonine, Tryptophan, Tyrosine and Valine.

An "Amino acid residue" is the unit in a peptide which comprises

—NH—CHR—COOH (C-terminal)

or $NH_2$—CHR—CO— (N-terminal)

or

—NH—CHR—CO— (internal)

where R is
H in Glycine,
$CH_3$ in Alanine,

OH in Serine,
CH₂SH in Cysteine,
CH(CH₃)CH₂CH₃ in Isoleucine,
CH₂CH(CH₃)₂ in Leucine
CH(CH₃)₂ in Valine
etc.

An "Amino acid side chain" is the R-group of an "Amino acid residue". For example, the R-group is
CH(CH₃)CH₂CH₃ in Isoleucine,
CH₂CH(CH₃)₂ in Leucine
CH(CH₃)₂ in Valine "Antibacterial activity" is any activity which inhibits the growth, metabolism or reproduction of bacteria, or increases the mortality of bacteria, or reduces the pathogenicity of bacteria.

The "positions" of the amino acid residues in Bacitracins are numbered from the N-terminal which can be Isoleucine, Valine or 5-Methylene-Isoleucine in position 1 (the left end in all figures showing Bacitracins in this application). Hence, Lys is in position number 6 and Asn is in position number 12.

In Bacitracins, the "position 1" is special, because this amino acid residue is partly incorporated into the Thiazoline ring. Thus the amino acid residue in position 1 in Bacitracins does not comprise the usual N-terminal unit:

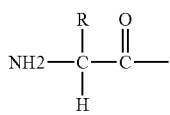

but comprises instead:

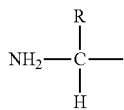

coupled to Thiazoline

A "composition" is any mixture comprising more than two different compounds, for example a mixture of two active pharmaceutical ingredients, or a mixture of an active pharmaceutical ingredient and one or more pharmaceutical excipients.

A "pharmaceutical composition" is any composition suitable for use in vivo. Such compositions can thus be administered cutaneously, subcutaneously, intravenously, parenterally etc.

5-Methylene-Isoleucine comprises two chiral carbon atoms which independently could be in R or S configuration.

The Bacitracins comprising at least one 5-Methylene-Isoleucine residue in position 1, 5 or 8 can be used for inhibiting unwanted bacterial growth both in vitro and in vivo. These compounds can thus have therapeutic effect if administered to an animal or a human with a bacterial infection.

The invention concerns the compound 5-Methylene-Isoleucine which could be used for production of the new Bacitracins; e.g. by in vitro synthesis of Bacitracin J1-3, K1-3 or L.

By substituting Isoleucine or Valine with 5-Methylene-Isoleucine in the methods described in J Org Chem, vol. 61 no. 12, 1996, page 3983-3986 by Lee et al or WO199747313, Bacitracins with antibacterial activity can be produced.

The invention is defined by the claims and not by the following illustrative examples:

EXAMPLES

Example 1

(2S,3R)-2-(1,3-Dioxo-1,3-dihydro-isoindol-2-yl)-3-methyl-hex-5-enoic acid methyl ester and (2S,3S)-2-(1,3-dioxo-1,3-dihydro-isoindol-2-yl)-3-methyl-hex-5-enoic acid methyl ester Vinylmagnesium bromide in THF (1.0 M, 83.64 mL, 83.64 mmol) is added to a precooled (−10° C.) mixture of (2S,3S) and (2S,3R)-4-Iodo-N-phataloylvaline methyl ester (26.96 g, 69.68 mmol), CuCl₂ (0.47 g, 3.5 mmol), dry LiCl (0.29 g, 7.0 mmol) in THF (100 mL). The reaction mixture is stirred overnight at this temperature. The reaction mixture is added to saturated ammonium chloride solution (aq) (300 mL). The phases are separated and the aqueous phase is extracted with diethyl ether (3×100 mL). The combined organic phases are washed with saturated brine (100 mL), dried (MgSO₄) and the solvents are removed at reduced pressure. 10 g of the product mixture is isolated The (2S,3S) and (2S,3R) products are separated by column chromatography.

Example 2

(2S,3R)-2-Amino-3-methyl-hex-5-enoic acid (2S,3R)-2-(1,3-Dioxo-1,3-dihydro-isoindol-2-yl)-3-methyl-hex-5-enoic acid methyl ester (2.01 g, 7.00 mmol) is dissolved in a 2:1 mixture of 6 N hydrochloric acid and glacial acetic acid (62.5 mL), and the solution is heated at reflux for 4 h. The solution is cooled to room temperature and concentrated under reduced pressure. The product is taken up in water and the solution is filtered. The filtrate is concentrated under reduced pressure and the residue is dissolved in water, then the solution is applied to a column of Amberlite™ IR 120 cation exchange resin (NH₄⁺ form.). The column is washed with water (2.5 L), then eluted with aqueous ammonia solution (2.5 L). The eluate is boiled until no ammonia can be detected, then concentrated under reduced pressure affording the title compound (0.5 g, 3.50 mmol).

Example 3

(2S,3S)-2-Amino-3-methyl-hex-5-enoic acid (2S,3S)-2-(1,3-Dioxo-1,3-dihydro-isoindol-2-yl)-3-methyl-hex-5-enoic acid methyl ester (2.01 g, 7.00 mmol) is dissolved in a 2:1 mixture of 6 N hydrochloric acid and glacial acetic acid (62.5 mL), and the solution is heated at reflux for 4 h. The solution is cooled to room temperature and concentrated under reduced pressure. The product is taken up in water and the solution is filtered. The filtrate is concentrated under reduced pressure and the residue is dissolved in water, then the solution is applied to a column of Amberlite™ IR 120 cation exchange resin (NH₄⁺ form.). The column is washed with water (2.5 L), then eluted with aqueous ammonia solution (2.5 L). The eluate is boiled until no ammonia can be detected, then concentrated under reduced pressure affording the title compound (0.5 g, 3.50 mmol).

Example 4

(2R,3R)-2-(1,3-Dioxo-1,3-dihydro-isoindol-2-yl)-3-methyl-hex-5-enoic acid methyl ester and (2R,3S)-2-(1,3-dioxo-1,3-dihydro-isoindol-2-yl)-3-methyl-hex-5-enoic acid methyl ester Vinylmagnesium bromide in THF (1.0 M, 83.64 mL, 83.64 mmol) is added to a precooled (−10° C.) mixture of (2S,3S) and (2S,3R)-4-Iodo-N-phataloylvaline methyl ester (26.96 g, 69.68 mmol), CuCl$_2$ (0.47 g, 3.5 mmol), dry LiCl (0.29 g, 7.0 mmol) in THF (100 mL). The reaction mixture is stirred over night at this temperature. The reaction mixture is added to saturated ammonium chloride solution (aq) (300 mL). The phases are separated and the aqueous phase is extracted with diethyl ether (3×100 mL). The combined organic phases are washed with saturated brine (100 mL), dried (MgSO$_4$) and the solvents are removed at reduced pressure. 10 g of the product mixture is isolated. The (2R,3S) and (2R,3R) products are separated by column chromatography.

Example 5

(2R,3R)-2-Amino-3-methyl-hex-5-enoic acid (2R,3R)-2-(1,3-Dioxo-1,3-dihydro-isoindol-2-yl)-3-methyl-hex-5-enoic acid methyl ester (2.01 g, 7.00 mmol) is dissolved in a 2:1 mixture of 6 N hydrochloric acid and glacial acetic acid (62.5 mL), and the solution is heated at reflux for 4 h. The solution is cooled to room temperature and concentrated under reduced pressure. The product is taken up in water and the solution is filtered. The filtrate is concentrated under reduced pressure and the residue is dissolved in water, then the solution is applied to a column of Amberlite™ IR 120 cation exchange resin (NH$_4^+$ form.). The column is washed with water (2.5 L), then eluted with aqueous ammonia solution (2.5 L). The eluate is boiled until no ammonia can be detected, then concentrated under reduced pressure affording the title compound (0.5 g, 3.50 mmol).

Example 6

(2R,3S)-2-Amino-3-methyl-hex-5-enoic acid (2R,3S)-2-(1,3-Dioxo-1,3-dihydro-isoindol-2-yl)-3-methyl-hex-5-enoic acid methyl ester (2.01 g, 7.00 mmol) is dissolved in a 2:1 mixture of 6 N hydrochloric acid and glacial acetic acid (62.5 mL), and the solution is heated at reflux for 4 h. The solution is cooled to room temperature and concentrated under reduced pressure. The product is taken up in water and the solution is filtered. The filtrate is concentrated under reduced pressure and the residue is dissolved in water, then the solution is applied to a column of Amberlite™ IR 120 cation exchange resin (NH$_4^+$ form.). The column is washed with water (2.5 L), then eluted with aqueous ammonia solution (2.5 L). The eluate is boiled until no ammonia can be detected, then concentrated under reduced pressure affording the title compound (0.5 g, 3.50 mmol).

The invention claimed is:

1. The compound 2-amino-3-methyl-hex-5-enoic acid.
2. A compound according to claim 1 having (2S,3S) configuration.
3. A compound according to claim 1 having (2R,3S) configuration.
4. A compound according to claim 1 having (2S,3R) configuration.
5. A compound according to claim 1 having (2R,3R) configuration.
6. A method of producing a compound according to claim 1, comprising a cross coupling of a vinyl Grignard agent with valine having a halide in 4-position.
7. The method according to claim 6, where the cross coupling is catalyzed by Li$_2$CuCl$_4$.
8. A method of producing a compound according to claim 1, comprising the following steps:
   (a) coupling a vinyl Grignard reagent with 4-Iodo-N-phathaloylvaline methyl ester to form 2-(1,3-dioxo-1,3-dihydroisoindol-2-yl)-3-methyl-hex-5-enoic acid methyl ester,
   (b) cleaving the methyl ester moiety to generate the corresponding carboxylic acid; and
   (c) deprotecting the alpha-amino group of 2-amino-3-methyl-hex-5-enoic acid.

* * * * *